United States Patent
Jeyachandran et al.

(10) Patent No.: US 12,133,945 B2
(45) Date of Patent: Nov. 5, 2024

(54) PERITONEAL DIALYSIS CYCLER HAVING DUAL PERISTALTIC PUMPS

(71) Applicants: BAXTER INTERNATIONAL INC., Deerfield, IL (US); BAXTER HEALTHCARE SA, Glattpark (CH)

(72) Inventors: Ramkumar Jeyachandran, Bangalore (IN); Vinayaka Hm, Karnataka (IN); Marcello Malagoli, Medolla (IT); Anoop Thirumattathil Ashokan, Alappuzha (IN)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 0 days.

(21) Appl. No.: 18/692,107

(22) PCT Filed: Aug. 30, 2022

(86) PCT No.: PCT/US2022/042031
§ 371 (c)(1),
(2) Date: Mar. 14, 2024

(87) PCT Pub. No.: WO2023/043612
PCT Pub. Date: Mar. 23, 2023

(65) Prior Publication Data
US 2024/0261483 A1     Aug. 8, 2024

(30) Foreign Application Priority Data
Sep. 14, 2021 (IN) .............................. 202141041240

(51) Int. Cl.
*A61M 1/28* (2006.01)
*A61M 39/10* (2006.01)

(52) U.S. Cl.
CPC ............ *A61M 1/281* (2014.02); *A61M 1/284* (2014.02); *A61M 39/10* (2013.01);
(Continued)

(58) Field of Classification Search
CPC ...... A61M 1/281; A61M 1/284; A61M 39/10; A61M 2202/0007; A61M 2202/0014; A61M 2202/04; A61M 2205/106
(Continued)

(56) References Cited

U.S. PATENT DOCUMENTS

| | | |
|---|---|---|
| 2007/0278155 A1 | 12/2007 | Lo et al. |
| 2013/0228517 A1* | 9/2013 | Roger ................ A61M 1/1613 604/29 |
| 2019/0307939 A1* | 10/2019 | Lo .......................... G01G 17/04 |

FOREIGN PATENT DOCUMENTS

WO       8402277       6/1984

OTHER PUBLICATIONS

Search Report issued in International Patent Application No. PCT/US2022042031 mailed on Jan. 30, 2023—7 pages.
(Continued)

*Primary Examiner* — Phillip A Gray
(74) *Attorney, Agent, or Firm* — K&L Gates LLP

(57) ABSTRACT

A disposable set for a peritoneal dialysis ("PD") treatment includes a fresh PD fluid pumping portion (118a): a used PD fluid pumping portion (118b): a reusable tubing section (124f) including the fresh PD fluid pumping portion (118a) and a one-way valve (132), the reusable tubing section terminating at a first connector; and a disposable tubing section (124u) including the used PD fluid pumping portion (118b) and terminating at a second connector, the second connector configured to be connected to the first connector to form the disposable set for use in the PD treatment.

21 Claims, 9 Drawing Sheets

(52) U.S. Cl.
CPC ............... *A61M 2202/0007* (2013.01); *A61M 2202/0014* (2013.01); *A61M 2202/04* (2013.01); *A61M 2205/106* (2013.01); *A61M 2205/127* (2013.01); *A61M 2205/128* (2013.01); *A61M 2205/3327* (2013.01); *A61M 2205/3334* (2013.01); *A61M 2205/36* (2013.01); *A61M 2209/06* (2013.01)

(58) Field of Classification Search
USPC .......................................................... 604/29
See application file for complete search history.

(56) References Cited

OTHER PUBLICATIONS

Written Opinion issued in International Patent Application No. PCT/US2022042031 mailed on Jan. 30, 2023—11 pages.
IPRP issued in International Patent Application No. PCT/US2022042031 mailed on Jan. 30, 2023—8 pages.

\* cited by examiner

PERITONEAL DIALYSIS CYCLER HAVING DUAL PERISTALTIC PUMPS

PRIORITY CLAIM

The present application is a national phase entry of PCT Patent Application No. PCT/US2022/042031, filed on Aug. 30, 2022, which claims priority to and the benefit of Indian Provisional Application No. 202141041240, filed Sep. 14, 2021, the entire contents of which are herein incorporated by reference and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an APD machine that reduces disposable waste.

SUMMARY

Known automated peritoneal dialysis ("PD") systems typically include a machine or cycler that accepts and actuates a pumping cassette having a hard part and a soft part that is deformable for performing pumping and valving operations. The hard part is attached to tubes that extend to various bags. The disposable cassette and associated tubes and bags can be cumbersome for a patient at home to load for treatment. The overall amount of disposable items may also lead to multiple setup procedures requiring input from the patient, which can expose room for error.

In a first main feature of the present disclosure, the APD system and associated methodology includes a cycler having a three-way valve that selects between primary fresh peritoneal dialysis ("PD") fluid and a last fill fluid. The cycler also includes a fresh PD fluid valve, which controls whether or not fresh dialysis fluid is able to flow to a patient. The cycler further includes a patient valve, which also controls whether or not fresh and used dialysis fluid is able to flow respectively to and from the patient. The fresh PD fluid and patient valves may be two-way valves.

The cycler includes a fresh PD fluid pump located downstream from the three-way valve and a used PD fluid pump located downstream from the patient valve. The PD fluid pumps may be peristaltic pumps or other types of pumps that operate with a disposable set, such as volumetric membrane or diaphragm pumps. In an embodiment, the cycler includes an inline heater positioned between the fresh PD fluid pump and the fresh PD fluid valve. A fresh PD fluid pressure transducer is in one embodiment located between an outlet of the fresh PD fluid pump and the inline heater for sensing and controlling positive pressure of fresh PD fluid delivered to the patient during a patient fill. A used PD fluid pressure transducer is in one embodiment located between the patient valve and an inlet of the used PD fluid pump for sensing and controlling negative pressure of used PD fluid removed from the patient during a patient drain. The cycler may further include one or more priming sensor, e.g., an ultrasonic sensor, positioned to determine if the disposable set is fully primed for treatment. The cycler may still further include a flow sensor operable with a patient line to sense and help control patient fill and drain flowrates and volumes.

The cycler operates with a disposable set, which includes multiple primary solution lines and a last fill line for connecting to multiple primary solution containers and a last fill container, respectively. The disposable set in an alternative embodiment also includes the multiple primary solution and last fill containers. The multiple primary solution lines and a last fill line operate with the three-way valve when the disposable set is loaded into or onto the cycler for operation. Similarly, fresh and used PD fluid pumping portions or segments, e.g., peristaltic tube segments, may be provided to operate with the fresh and used PD fluid pumps, respectively. The disposable set may also be provided with an inline fluid heating pathway, e.g., serpentine heating pathway, for operating with the inline heater.

The disposable set includes fresh and used PD fluid pressure pods, which operate respectively with the fresh and used PD fluid pressure transducers. The pressure pods in an embodiment include a housing having a sealed diaphragm that separates the housing into a PD fluid receiving side and an air side. Fresh and used PD fluid fills the fluid sides of fresh and used PD fluid pressure pods, respectively. The pressure exerted by the fresh and used PD fluid is transmitted via the diaphragm to the air side of the housing, which is in sealed pneumatic communication with one of fresh and used PD fluid pressure transducers of the cycler. The air pressure in the sealed air side of the housing equalizes with and is the same (positive or negative) as the fluid pressure. The air pressure is detected by the contacted pressure transducer.

In an embodiment, when the disposable set is mounted for operation, the fresh PD fluid valve operates with a line exiting the inline heater upstream of a "Y" or "T" split, wherein a drain line of the disposable set extends from one leg of the "Y" or "T" split and includes the used PD fluid pumping portion or segment. A patient line extends from another leg of the "Y" or "T" split and operates with the patient valve, which controls whether or not fresh and used dialysis fluid is able to flow respectively to and from the patient.

To further reduce disposable waste and cost, it is contemplated to make a section of the disposable set reusable. It is desirable to reuse as much of the disposable set as possible, which may be determined by reusing any portion of the disposable set that does not contact used dialysis fluid or patient effluent. It is accordingly contemplated to divide the disposable set in the fresh dialysis fluid line just upstream of the "Y" or "T" split. In this manner, a reusable tubing section may include the inline fluid heating pathway, the solution and last fill lines, saving a large portion of the disposable set from having to be discarded after every treatment. The discarded portion may be termed the disposable tubing section.

To create the reusable and disposable tubing sections, a post-heating pathway segment of the disposable set is split into two sub-segments, namely, a fresh, reusable sub-segment and a used, disposable sub-segment. The fresh, reusable sub-segment terminates with a one-way male luer lock check valve, while the used, disposable sub-segment terminates with a female luer lock connector. The female luer lock connector is connected to the one-way male luer lock check valve prior to treatment to form the disposable set for operation with the cycler.

A packaging assembly for the partially reusable disposable set is provided, wherein the reusable tubing section is provided within a first sealed container. The disposable tubing section of the disposable set is provided within a second sealed container. The sealed first and second containers may be packaged together in an overpouch and sterilized via steam, gamma radiation or ethylene oxide. In a first use, the sterilized containers are opened, a cap is removed from female luer lock connector, after which the one-way male luer lock check valve and the female luer lock connector are connected to form the partially reusable disposable set for use with a cycler.

After treatment, the patient or caregiver uses a heat sealer to cut, seal and remove the disposable tubing section from the reusable tubing section, while leaving the reusable tubing section sealed and sterilized. In a subsequent treatment, a replacement packaging assembly is opened, wherein the replacement package has only the disposable tubing section of the disposable set. The replacement packaging may then be provided with a smaller overpouch. The patient removes the old female luer lock connector (connected to sealed tubing) from the reusable one-way male luer lock check valve and connects the new female luer lock connector from the new disposable tubing section to form a new overall disposable set for the next treatment.

In an alternative APD system of the present disclosure, the inline tubing heating pathway is replaced by a batch heater that heats the fresh PD fluid containers or bags and the last fill container or bag. The heater and containers may be provided in an enclosure that efficiently heats the dialysis fluid inside the containers to body temperature or 37° C. In this alternative embodiment, and in any of the systems described herein, one or more components that are normally reusable are made instead to be disposable, or have disposable components, reducing the amount of hardware needed. One such component includes the fresh and used PD fluid pumps, which may be peristaltic pumps wherein the pump rollers and raceways are hard plastic and disposable. The disposable rollers are then conveniently coupled to the output shaft of a reusable motor for treatment. The arrangement thus allows the user to load the disposable for treatment without having to handle peristaltic pump tubing. Another such component is a flow sensor, which may include a disposable rotor, vane or fan blade that spins within a section of the patient line at a rate dependent on the flowrate of fresh or used PD fluid flowing through the patient line. The outputs from the flow sensor are used to control the flowrate of fresh and used PD fluid pumped by the fresh and used PD fluid pumps to achieve desired or specified flowrates. A further component may include a disposable conductivity sensor placed along the patient line, the output of which may be (i) compared to a desired conductivity output to ensure that fresh PD fluid is of the prescribed constituency and (ii) used to measure urea and creatinine levels and potential peritonitis of the used PD fluid. A still further disposable component may be a disposable pressure sensor, which may for example be a disposable PD fluid pressure pod.

In a further alternative embodiment, the cycler includes a single PD fluid pump, which pumps both fresh and used PD fluid. In the single pump embodiment, a first three-way valve may be provided again to select between primary fresh PD fluid and a last fill fluid for a patient fill. A second three-way valve is provided to allow either the flow of fresh PD fluid through a fresh, pre-pump line to a pumping segment of the PD fluid pump or the flow of used PD fluid through a used pre-pump line to the pumping segment. A third three-way valve is provided to allow either the flow of used PD fluid from the pumping segment, through a drain line, to a drain container or house drain or the flow of fresh PD fluid from the pumping segment, through a fresh, post-pump line, to an inline fluid heating pathway. A fourth three-way valve is provided to allow either the flow of fresh PD fluid from the inline fluid heating pathway, through the post-heating pathway segment, to the patient line or the flow of used PD fluid from the patient and the patient line, through the used pre-pump, back to the second three-way valve.

In light of the disclosure set forth herein, and without limiting the disclosure in any way, in a first aspect of the present disclosure, which may be combined with any other aspect, or portion thereof, a disposable set for a peritoneal dialysis ("PD") treatment incudes a fresh PD fluid pumping portion: a used PD fluid pumping portion: a reusable tubing section including the fresh PD fluid pumping portion and a one-way valve, the reusable tubing section terminating at a first connector; and a disposable tubing section including the used PD fluid pumping portion and terminating at a second connector, the second connector configured to be connected to the first connector to form the disposable set for use in the PD treatment.

In a second aspect of the present disclosure, which may be combined with any other aspect, or portion thereof, at least one of the fresh PD fluid pumping portion or the used PD fluid pumping portion includes a tubing segment for operation with a peristaltic pump actuator.

In a third aspect of the present disclosure, which may be combined with any other aspect, or portion thereof, the disposable set includes at least one supply line located on an opposing side of the fresh PD fluid pumping portion from the one-way valve and the first connector.

In a fourth aspect of the present disclosure, which may be combined with any other aspect, or portion thereof, the disposable set includes a first "Y" or "T" connection between first and second supply lines and a second "Y" or "T" connection between an outlet line of the first "Y" or "T" connection and a third supply line.

In a fifth aspect of the present disclosure, which may be combined with any other aspect, or portion thereof, the disposable set includes first and second primary fresh PD fluid containers in fluid communication with the first and second supply lines and a last fill fluid container in fluid communication with the third supply line.

In a sixth aspect of the present disclosure, which may be combined with any other aspect, or portion thereof, at least one of (i) the reusable tubing section includes a fresh PD fluid pressure sensing area in fluid communication with the fresh PD fluid pumping portion or (ii) the disposable tubing section includes a used PD fluid pressure sensing area in fluid communication with the used PD fluid pumping portion.

In a seventh aspect of the present disclosure, which may be combined with any other aspect, or portion thereof, the at least one fresh PD fluid pressure sensing area or the used PD fluid pressure sensing area includes a pressure pod having a diaphragm separating a PD fluid receiving side from an air side of the pod.

In an eighth aspect of the present disclosure, which may be combined with any other aspect, or portion thereof, at least one of the fresh PD fluid pressure sensing area is in fluid communication with an outlet of the fresh PD fluid pumping portion, or the used PD fluid pressure sensing area is in fluid communication with an inlet of the used PD fluid pumping portion.

In a ninth aspect of the present disclosure, which may be combined with any other aspect, or portion thereof, the reusable tubing section includes an inline fluid heating pathway.

In a tenth aspect of the present disclosure, which may be combined with any other aspect, or portion thereof, the inline fluid heating pathway is a serpentine pathway.

In an eleventh aspect of the present disclosure, which may be combined with any other aspect, or portion thereof, the disposable tubing section includes a drain line in fluid communication with an outlet of the used PD fluid pumping portion.

In a twelfth aspect of the present disclosure, which may be combined with any other aspect, or portion thereof, the disposable set includes a drain container in fluid communication with the drain line.

In a thirteenth aspect of the present disclosure, which may be combined with any other aspect, or portion thereof, the disposable tubing section includes a patient line.

In a fourteenth aspect of the present disclosure, which may be combined with any other aspect, or portion thereof, the disposable set includes a packaging assembly including a first sealed container holding the reusable tubing section a second sealed container holding the disposable tubing section.

In a fifteenth aspect of the present disclosure, which may be combined with any other aspect, or portion thereof, the disposable set includes a replacement packaging assembly providing the second sealed container but not the first sealed container.

In a sixteenth aspect of the present disclosure, which may be combined with any other aspect, or portion thereof, a peritoneal dialysis ("PD") system comprises a disposable set including a fresh PD fluid pumping portion, a used PD fluid pumping portion, a reusable tubing section including the fresh PD fluid pumping portion and a one-way valve, the reusable tubing section terminating at a first connector, and a disposable tubing section including the used PD fluid pumping portion and terminating at a second connector, the second connector configured to be connected to the first connector to form the disposable set for use in the PD treatment; and a cycler including a fresh PD fluid pump operable with the fresh PD fluid pumping portion, and a used PD fluid pump operable with the used PD fluid pumping portion.

In a seventeenth aspect of the present disclosure, which may be combined with any other aspect, or portion thereof, the reusable tubing section includes a fresh PD fluid pressure pod and the disposable tubing section includes a used PD fluid pressure pod, and wherein the cycler includes fresh and used PD fluid pressure transducers operable with the fresh and used PD fluid pressure pods, respectively.

In an eighteenth aspect of the present disclosure, which may be combined with any other aspect, or portion thereof, the reusable tubing section includes an inline fluid heating pathway, and the cycler includes an inline heater operable with the inline fluid heating pathway.

In a nineteenth aspect of the present disclosure, which may be combined with any other aspect, or portion thereof, the cycler includes at least one priming sensor operable with the disposable tubing section.

In a twentieth aspect of the present disclosure, which may be combined with any other aspect, or portion thereof, the cycler includes at least one first valve operable with the reusable tubing section upstream of the fresh PD fluid pumping portion, the cycler further including at least one second valve operable with the disposable tubing section upstream of the used PD fluid pumping portion.

In a twenty-first aspect of the present disclosure, which may be combined with any other aspect, or portion thereof, the cycler includes a flow sensor operable with a patient line portion of the disposable tubing section.

In a twenty-second aspect of the present disclosure, which may be combined with any other aspect, or portion thereof, a peritoneal dialysis ("PD") system comprises a disposable set including a primary solution line, a fresh and used PD fluid pumping portion located downstream from the primary solution line, a patient line in two-way fluid communication with the fresh and used PD fluid pumping portion, a drain line located downstream from the patient line, and a used PD fluid line in fluid communication with the patient line and an inlet to the fresh and used PD fluid pumping portion; and a cycler including a fresh and used PD fluid pump operable with the fresh and used PD fluid pumping portion.

In a twenty-third aspect of the present disclosure, which may be combined with any other aspect, or portion thereof, the disposable set includes a last fill line, the fresh and used PD fluid pumping portion located downstream from the last fill line, and wherein the cycler includes at least one valve for selectively opening the primary solution line or the last fill line.

In a twenty-fourth aspect of the present disclosure, which may be combined with any other aspect, or portion thereof, the PD system includes at least one valve for selectively opening a PD fluid line extending between the primary solution line and the fresh and used PD fluid pumping portion or the used PD fluid line.

In a twenty-fifth aspect of the present disclosure, which may be combined with any other aspect, or portion thereof, the PD system includes at least one valve for selectively opening the drain line or a PD fluid line extending between the fresh and used PD fluid pumping portion and the patient line.

In a twenty-sixth aspect of the present disclosure, which may be combined with any other aspect, or portion thereof, the PD system includes at least one valve for selectively opening the patient line or the used PD fluid line.

In a twenty-seventh aspect of the present disclosure, which may be combined with any other aspect, or portion thereof, a peritoneal dialysis ("PD") system comprises a disposable set including a fresh PD fluid pumping portion including a first disposable set of rollers, a used PD fluid pumping portion including a second disposable set of rollers, a patient line in fluid communication with the fresh and used PD fluid pumping portions, and at least one of a flowmeter disposable, a conductivity sensor disposable or a pressure sensor disposable located along the patient line; and a cycler including a fresh pump motor operable with the first disposable set of rollers, a used pump motor operable with the second disposable set of rollers, and at least one of a flowmeter detector operable with the flowmeter disposable, a conductivity detector operable with the conductivity sensor disposable, or a pressure transducer operable with the pressure sensor disposable.

In a twenty-eighth aspect of the present disclosure, which may be combined with any other aspect, or portion thereof, at least one of the fresh and used PD fluid pumping portions includes a disposable raceway.

In a twenty-ninth aspect of the present disclosure, which may be combined with any other aspect, or portion thereof, the flowmeter disposable includes a rotating rotor and the flowmeter detector includes a rotor detector.

In a thirtieth aspect of the present disclosure, which may be combined with any other aspect, or portion thereof, the conductivity sensor disposable includes at least one probe having a conductive electrode, and wherein the conductivity detector includes at least one electrical contact for electrical communication with the at least one conductive electrode.

In a thirty-first aspect of the present disclosure, which may be combined with any other aspect, or portion thereof, the pressure sensor disposable includes a PD fluid pressure pod.

In a thirty-second aspect of the present disclosure, which may be combined with any other aspect, or portion thereof, any of the features, functionality and alternatives described in connection with any one or more of FIGS. 1 to 9 may be combined with any of the features, functionality and alternatives described in connection with any other of FIGS. 1 to 9.

It is accordingly an advantage of the present disclosure to provide an automated peritoneal dialysis ("APD") machine or cycler that achieves relatively precise pressure control.

It is another advantage of the present disclosure to provide an APD cycler that reduces disposable cost.

It is yet another advantage of the present disclosure to provide an APD cycler that is relatively quiet.

It is still another advantage of the present disclosure to provide an APD cycler that is reuses a portion of the disposable set.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

First Cycler Embodiment

Figure 1:
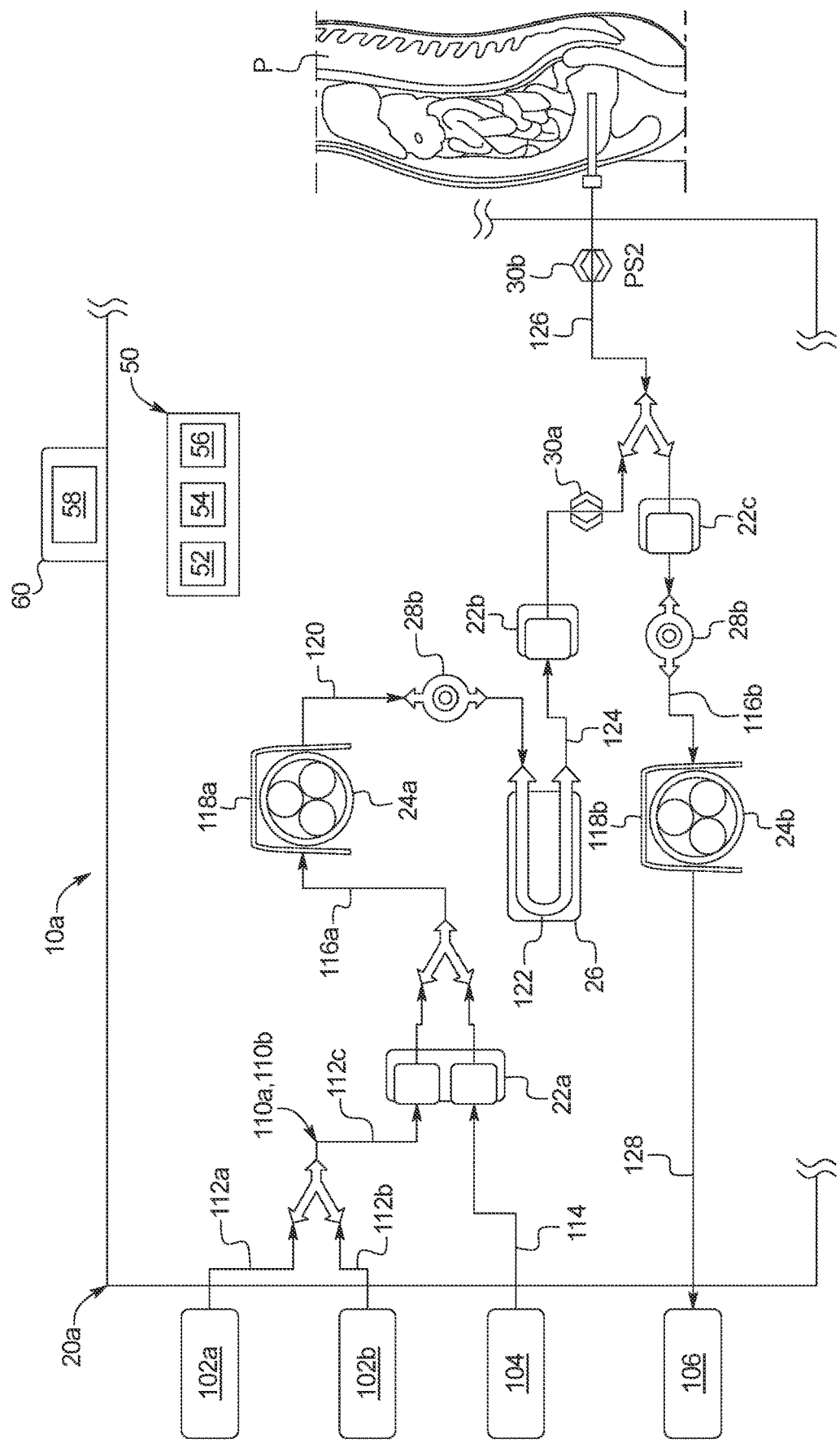
FIG. 1 is a flow schematic view of a first automated peritoneal dialysis ("APD") system of the present disclosure having a dual peristaltic pump arrangement.

Referring now to the drawings and in particular to FIG. 1, a first primary embodiment of an automated peritoneal dialysis ("APD") system 10a and associated methodology of the present disclosure includes an APD machine or cycler 20a. In the illustrated embodiment, APD machine or cycler 20a includes an inlet valve 22a, which may be a three-way valve that selects between primary fresh peritoneal dialysis ("PD") fluid and a last fill fluid. Cycler 20a includes a fresh PD fluid valve 22b, which controls whether or not fresh dialysis fluid is able to flow to a patient P. Cycler 20a also includes a patient valve 22c, which controls whether or not used dialysis fluid is able to flow to or from patient P.

Cycler 20a also includes a fresh PD fluid pump 24a, which in the illustrated embodiment is a peristaltic pump. Cycler 20a further includes a used PD fluid pump 24b, which in the illustrated embodiment is also a peristaltic pump. Fresh and used peristaltic dialysis fluid pumps 24a and 24b may be unidirectional or pump in two directions. Even though peristaltic PD fluid pumps 24a and 24b only need to operate in a single direction to deliver fresh dialysis fluid to and remove used dialysis fluid from the patient, respectfully, it may be desirable for PD fluid pumps 24a and 24b to be two-way pumps, e.g., for priming purposes and to reverse the flow of improperly heated fresh PD fluid.

Cycler 20a provides an inline heater 26 downstream from fresh PD fluid pump 24a in the illustrated embodiment. Inline heater 26 is in one embodiment sized to be able to heat fresh PD fluid from, e.g., 10° C. to body temperature or 37° C., over flowrates ranging from, e.g., 50 ml/min to 300 ml/min. Inline heater 26 may include a flow through and/or circulation heater. Although not illustrated, one or more temperature sensor may be located downstream and possibly upstream from inline heater 26 for reading out relevant fluid temperatures at a user interface and for providing feedback to control inline heater 26 to maintain the dialysis fluid at a specified temperature. The one or more temperature sensor may be a thermocouple or thermistor for example.

Cycler 20a further includes a fresh PD fluid pressure transducer 28a and a used PD fluid pressure transducer 28b. The output of fresh PD fluid pressure sensor 28a is used as feedback to ensure that the positive pressure of fresh PD fluid delivered to patient P from fresh PD fluid pump 24a is within a positive patient pressure limit (e.g., 3.0 psig (0.21 bar) or less). The output of used PD fluid pressure sensor 24b is used as feedback to ensure that the negative pressure of used PD fluid removed from patient P via used PD fluid pump 24b is within a negative patient pressure limit (e.g., at or between −1.5 psig (−0.10 bar) and zero psig).

Cycler 20a further includes priming sensors 30a and 30b, which may be ultrasonic, capacitive, inductive, magnetic or other types of sensors able to discern dialysis fluid from air. Priming sensor 30a is positioned to sense whether a fluid heating pathway for inline heater 26 is fully primed with fresh PD fluid. Priming sensor 30b is positioned to sense whether the disposable set including a patient line has been fully primed with fresh PD fluid.

Although not illustrated in FIG. 1 (see FIG. 8 instead), cycler 20a may further include a fluid flow sensor, which is a capacitive, inductive, magnetic or other type of sensor capable of detecting a rotor, vane or baffle (analogous to fan blades) that spins within a section of the patient line at a rate dependent upon the flowrate of fresh or used PD fluid flowing through the patient line. The outputs from the flow sensor are used to control the flowrate of fresh and used PD fluid pumped by PD fluid pumps 24a and 24b to desired or specified flowrates. The outputs from the flow sensor are also integrated over time to yield (i) how much fresh PD fluid is delivered to patient P, (ii) how much used PD fluid is removed from patient P, and (iii) a difference between (ii) versus (i) to know how much ultrafiltration ("UF") or excess water has been removed from the patient.

In the illustrated embodiment of FIG. 1, each of valves 22a to 22c, pumps 24a and 24b, and heater 26 are powered and controlled via a control unit 50, which includes one or more processor 52, one or more memory 54 and a video controller 56 for controlling a video monitor 58. Video monitor 58 is part of an overall user interface 60 for each of systems 10a to 10d described herein. User interface 60 includes any one or more of a touch screen overlay operable with video monitor 58 and/or one or more electromechanical input device, e.g., membrane switches, for inputting information into control unit 50. Video monitor 58 and speakers (e.g., operable with a sound card of control unit 50) are provided to output information to the patient or user, e.g., alarms, alerts and/or voice guidance commands.

Similarly, each of pressure sensors 28a, 28b, priming sensors 30a, 30b, flow sensor (not illustrated) and one or more temperature sensor (not illustrated) outputs to control unit 50. Control unit 50 uses the sensor outputs to control and monitor the components and their functions for each of systems described herein. Control unit 50 is programmed to run any of the flow sequences for systems 10a to 10d described herein. Control unit 50 may also include a transceiver and a wired or wireless connection to a network, e.g., the internet, for sending treatment data to and receiving prescription instructions from a doctor's or clinician's server interfacing with a doctor's or clinician's computer.

Figure 2:
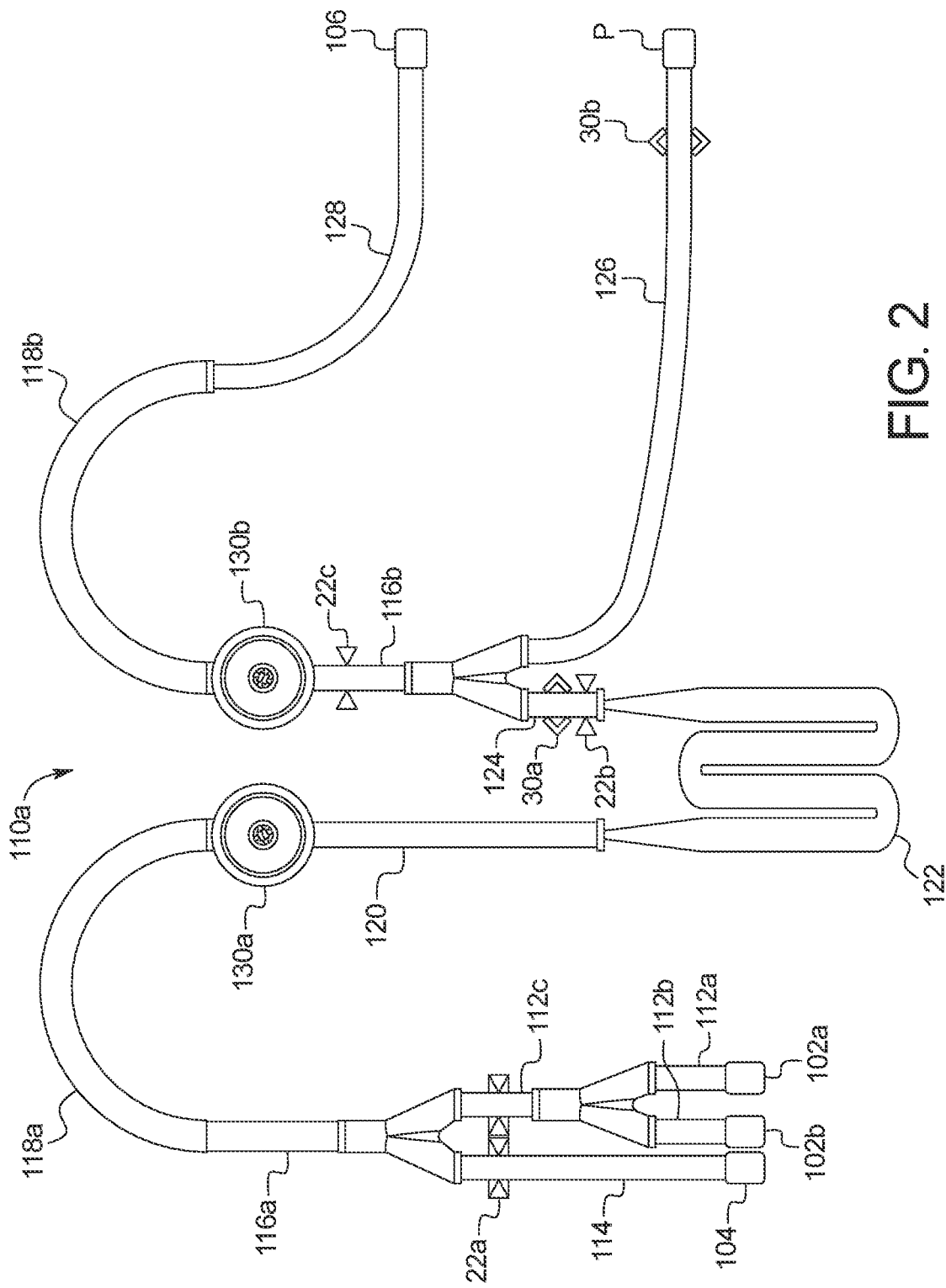
FIG. 2 is an elevation or top plan view of one embodiment of a disposable set useable with the system of FIG. 1.

FIGS. 1 and 2 illustrate that cycler 20a operates with a disposable set 110a. FIG. 1 illustrates that system 10a includes primary fresh PD fluid containers or bags 102a and 102b and a last fill container or bag 104 which are connected (e.g., spiked or luer fitting connected) to primary solution lines 112a and 112b and last fill solution line 114, respectively, of disposable set 110a. Primary fresh PD fluid containers or bags 102a and 102b may each be one to six liter bags of the primary fresh PD fluid used for treatment. Primary fresh PD fluid containers or bags 102a and 102b may hold the same or different glucose level fresh PD fluid, which may be a standard level such as 1.36% glucose PD fluid or 2.27% glucose PD fluid. Last fill container or bag 104 in an embodiment holds a single fill volume (e.g., one to two liters) of a last fill PD fluid, such as icodextrine. A drain 106 is provided, which may be a drain container or bag or a house drain, such as a toilet or bathtub. Containers 102a, 102b, 104 and 106 may or may not be provided as part of disposable set 110a and the other disposable sets described herein.

Primary solution lines 112a and 112b "Y" or "T" into a common primary solution line 112c. Common primary solution line 112c and last fill solution line 114 "Y" or "T" into fresh, pre-pump line 116a. Fresh, pre-pump line 116a extends to an inlet of fresh PD fluid pumping portion or segment 118a. A fresh, post-pump line 120 extends between an outlet of fresh pumping segment 118a and the inlet to an inline fluid heating pathway 122, which in the illustrated embodiment is a serpentine fluid heating pathway. A post-heating pathway segment 124 extends from the outlet of the serpentine fluid heating pathway 122 and "Y's" or "T's" with a patient line 126 and a used pre-pump line 116b. Used, pre-pump line 116b extends to an inlet of used PD fluid pumping portion or segment 118b. A drain line 128 extends from the outlet of used pumping segment 118b to drain 106, e.g., a drain container or house drain.

FIG. 2 illustrates fresh and used PD fluid pressure pods 130a and 130b, which operate respectively with fresh and used PD fluid pressure transducers 28a and 28b. Fresh and used PD fluid pressure pods 130a and 130b in one embodiment include a rigid housing that encloses a sealed diaphragm. The diaphragm separates the housing into a PD fluid receiving side and an air side. Fresh and used PD fluid fills the fluid sides of fresh and used PD fluid pressure pods 130a and 130b, respectively. The pressure exerted by the fresh and used PD fluid is transmitted via the diaphragm to the air side of the housing, which is in sealed pneumatic communication with one of fresh and used PD fluid pressure transducers 28a and 28b. The air pressure in the sealed air side of the housing equalizes with and is the same (positive or negative) as the fluid pressure. The air pressure is detected by the contacted pressure transducer 28a or 28b. FIG. 2 illustrates that fresh PD fluid pressure pod 130a is located along fresh, post-pump line 120 so as to detect a positive pressure formed via the actuation of fresh pumping segment 118a. Used PD fluid pressure pod 130b is located along used pre-pump line 116b so as to detect a negative pressure formed via the actuation of used pumping segment 118b. In an alternative embodiment, a single fresh and used pressure pod (not illustrated) is located along patient line 126 and is used to sense both positive and negative pressure for both patient filling and patient draining, respectively.

As illustrated in FIGS. 1 and 2, three-way valve 22a operates with common primary solution line 112c and last fill solution line 114. Although not illustrated, a second three-way valve may be similarly located to selectively open either primary solution line 112a or primary solution line 112b, for example, if primary fresh PD fluid containers or bags 102a and 102b contain different glucose level fresh PD fluids. In the illustrated embodiment fresh PD fluid pump 24a can pull from either PD fluid containers or bags 102a and 102b, or perhaps if one container is located on top of the other container, then primarily from the lower of the two containers until the lower container is empty.

FIGS. 1 and 2 illustrate that valve 22b and priming sensor 30a both operate with post-heating pathway segment 124. If cycler 20a is provided with a single temperature sensor (not illustrated), the temperature sensor may also be positioned to operate with post-heating pathway segment 124. If cycler 20a is provided with two temperature sensors, an upstream temperature sensor may be positioned to operate with fresh, post-pump line 120, while the downstream pressure sensor is positioned to operate with post-heating pathway segment 124. Priming sensor 30b is illustrated as operating at the end of patient line 126. Priming sensor 30b may be provided with a clip located on the outside of cycler 20a, which patient P or the caregiver uses to place and hold the distal end of patient line 126 prior to treatment. In this configuration, once priming sensor 30b detects fluid, the entire tubing set 110a is fully primed.

FIGS. 1 and 2 further illustrate that when patient valve 22c is closed and valve 22b is open, fresh, heated PD fluid may be pumped via fresh PD fluid pump 24a via patient line 126 to patient P. When patient valve 22c is open and valve 22b is closed, used PD fluid may be pumped via used PD fluid pump 24b from patient line 126, to drain line 128 to a drain container or bag of house drain 106.

It should therefore be appreciated that cycler 20a and disposable set 110a form an overall simple and inexpensive system 10a. Cycler 20a (and any of the cyclers discussed herein) may be made of metal, such as stainless steel, steel or aluminum and/or plastic, such as polyvinyl chloride ("PVC"), polyethylene ("PE"), polyurethane ("PU") and/or polycarbonate ("PC"). Disposable set 110a (and any of the disposable sets discussed herein) may be made of any of the plastics listed above. Fresh pumping segment 118a and used pumping segment 118b may be thickened and/or enlarged in diameter relative to the other lines and tubes and may be made of a material and shore hardness beneficial for peristaltic pumping.

Figure 3:
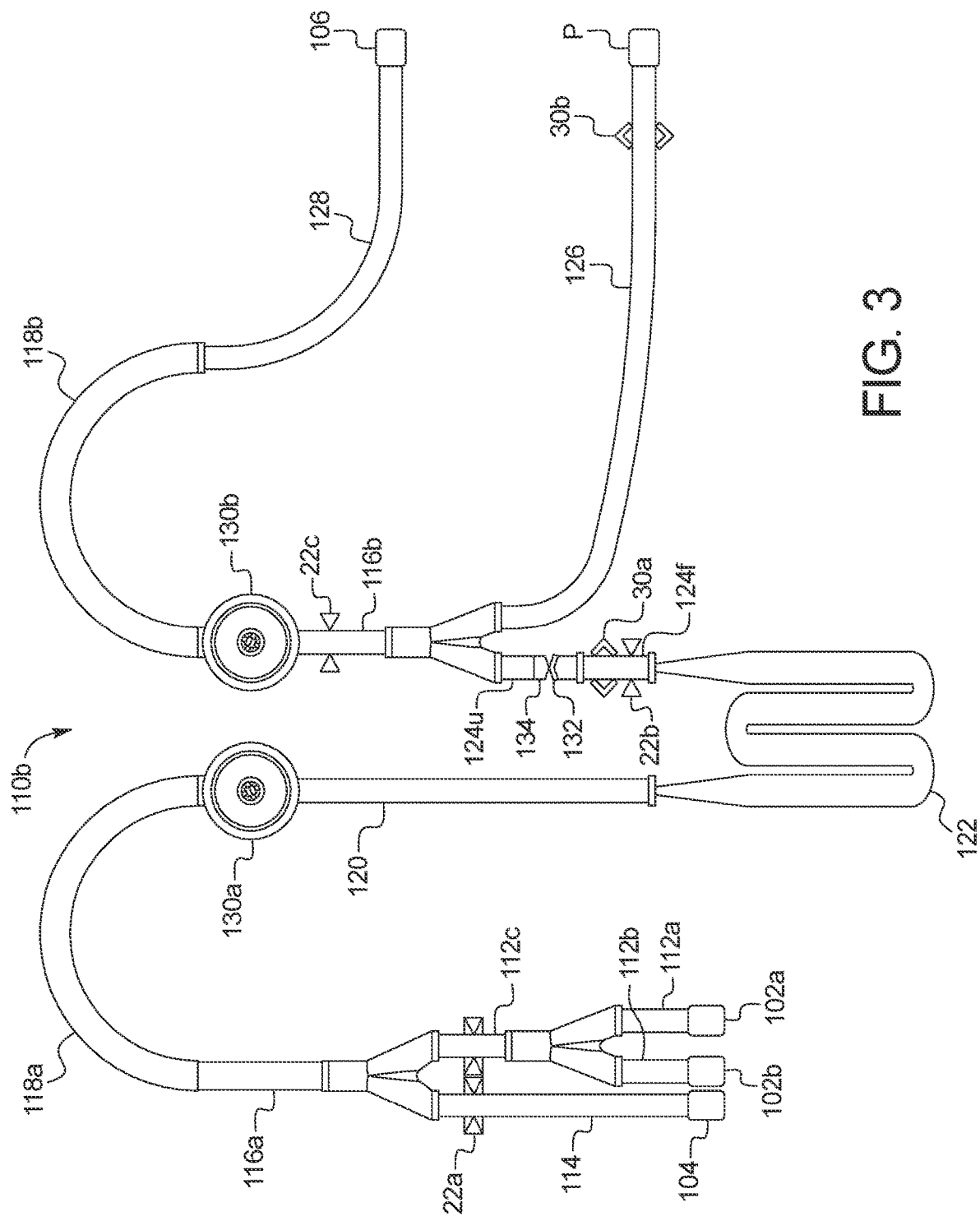
FIG. 3 is an elevation or top plan view of another embodiment of a disposable set useable with the system of FIG. 1.

Referring now to FIG. 3, an alternative disposable set 110b useable with cycler 20a of system 10a is illustrated. Disposable set 110b includes many of the same components as discussed above for disposable set 110a. Those components are numbered the same as above for disposable set 110a and include all of the structure, functionality and alternatives discussed above for set 110a. The primary difference is that post-heating pathway segment 124 is split into two segments, namely, a fresh, reusable sub-segment 124f and a used, disposable sub-segment 124u. Fresh, reusable sub-segment 124f terminates with a one-way male luer lock check valve 132, while used, disposable sub-segment 124u terminates with a female luer lock connector 134. Female luer lock connector 134 is connected to one-way male luer lock check valve 132 prior to treatment to form disposable set 110b for operation with cycler 20a, which may take place in the same manner as described above for disposable set 110a and cycler 20a.

During treatment, one-way male luer lock check valve 132 prevents used PD fluid or effluent pulled from patient P along patient line 128 from flowing up used, disposable sub-segment 124u and into fresh, reusable sub-segment 124f. The check valve or one-way valve may be for example a duck-billed one-way valve or check valve provided as part of the male luer lock connector or as a separate component from the male luer lock connector. Fresh, reusable sub-segment 124f and the lines upstream from same, including primary solution lines 112a and 112b, last fill solution line 114, fresh, pre-pump line 116a, fresh pumping segment 118a, fresh, post-pump line 120 and inline fluid heating pathway 122 are therefore each reusable. Each of those lines is kept intact after treatment, e.g., may be left in place loaded onto cycler 20a, and reused for multiple treatments.

Figure 4:
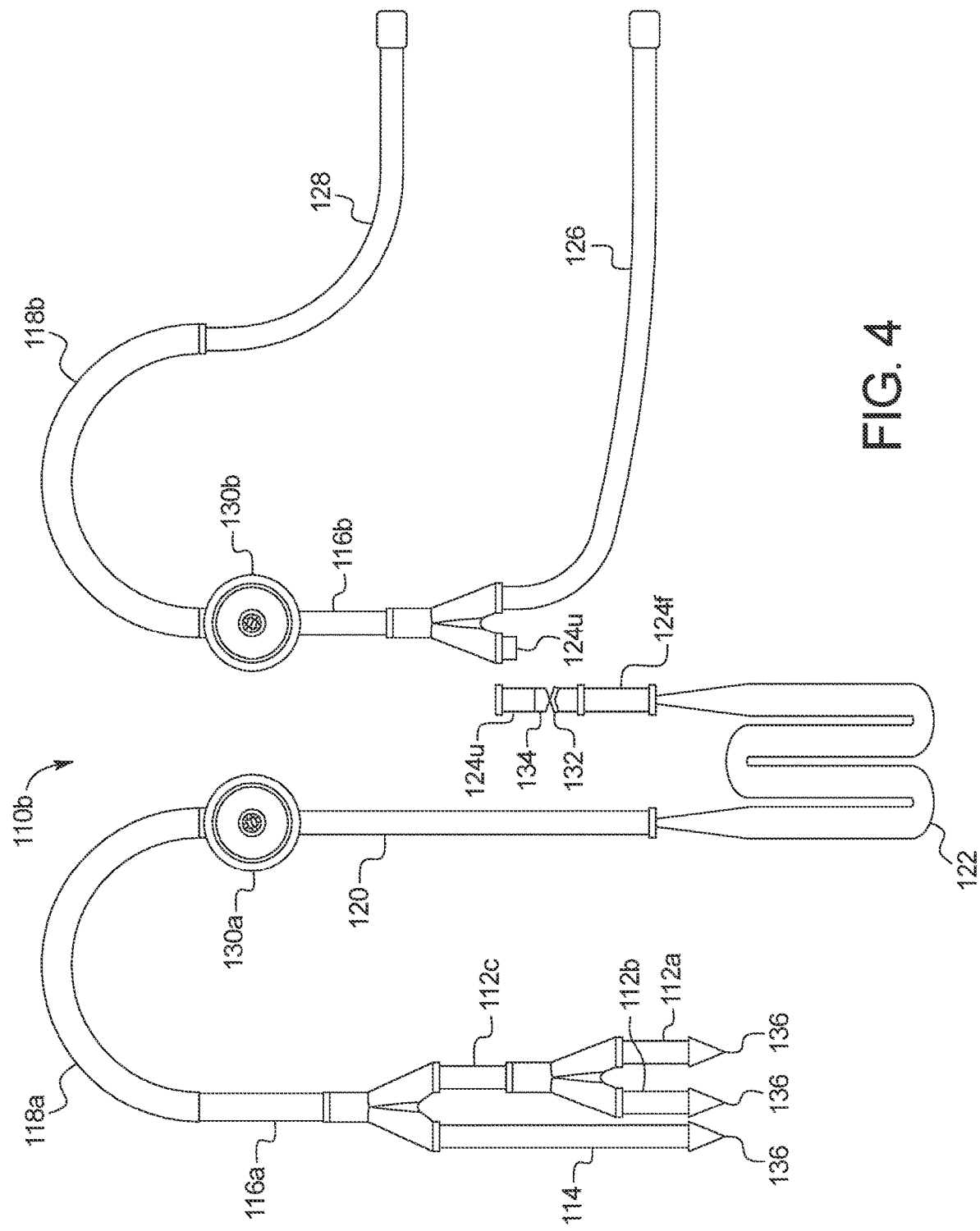
FIG. 4 is an elevation or top plan view of the disposable set of FIG. 3 having a disposable portion of same separate for removal.

FIG. 4 illustrates what happens to disposable set 110b after treatment. Here, patient P or a caregiver may use a commercially available handheld tube sealer and cutter after treatment to cut and heat seal closed the used, disposable sub-segment 124u downstream from the connection between male luer lock check valve 132 and female luer lock connector 134. Suitable handheld tube sealers and cutters include those provided by (i) Conroy Medical, Väsby, Sweden, under the tradename QsealR, and (ii) Lmb Technologie GmbH, Schwaig, Germany, under the tradename SEALmaticP™.

It is also contemplated to provide reusable solution lines 112a and 112b and last fill solution line 114 with spike connectors 136 at their ends. Spike connectors 136 translate into and out of primary fresh PD fluid containers or bags 102a and 102b and last fill container or bag 104. The patient may also be provided with an ultraviolet ("UV") connection chamber inside which spike connectors 136 are translatingly removed from used containers or bags 102a, 102b and 104 and respiked into new containers or bags 102a, 102b and 104 while being subjected to UV radiation.

Figure 5:
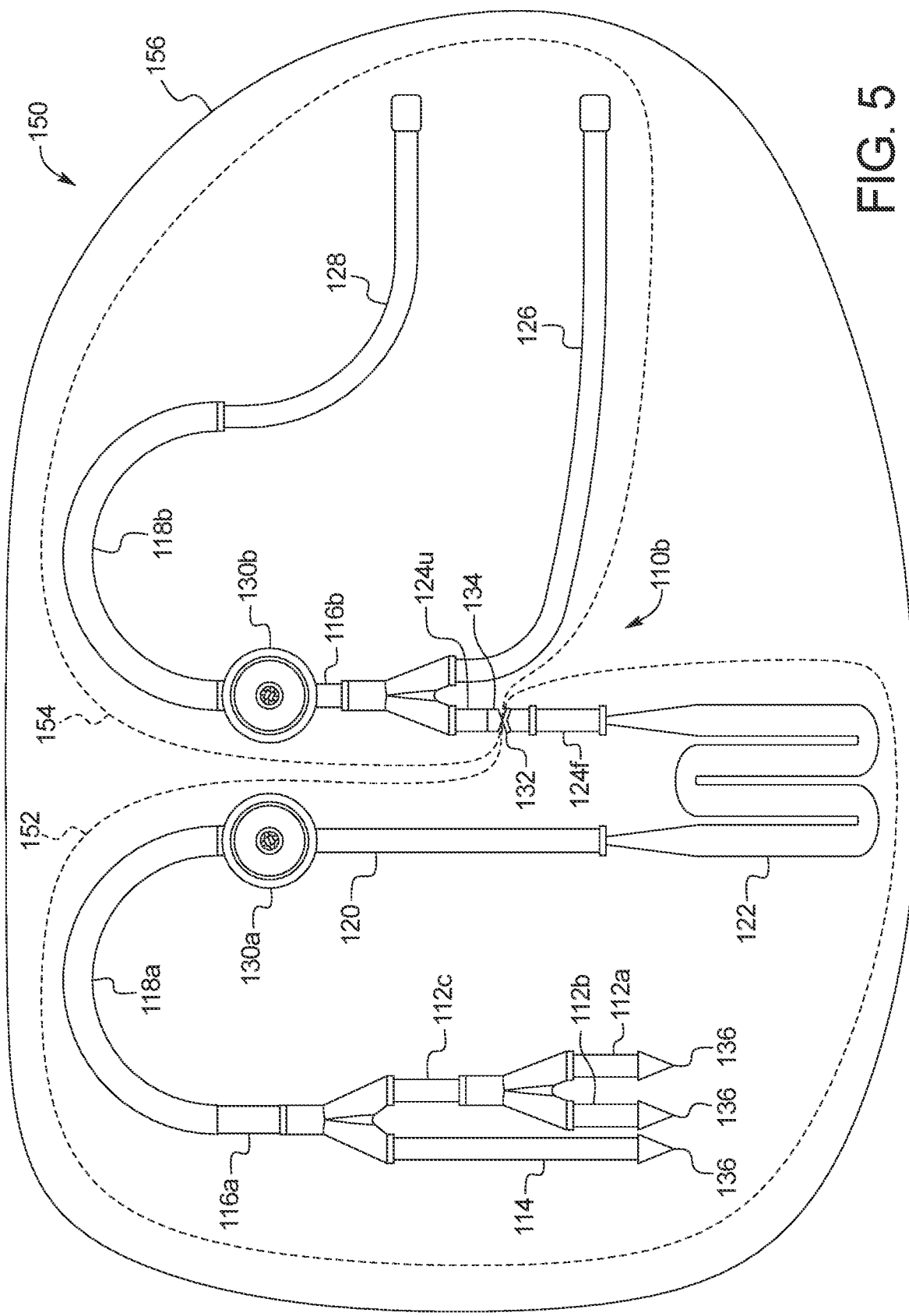
FIG. 5 is an elevation or top plan view of the disposable set of FIG. 3 in a packaging arrangement.

Referring now to FIG. 5, one embodiment of a packaging assembly 150 for partially reusable disposable set 110b is illustrated. As illustrated in FIG. 5, the reusable tubing section of disposable set 110b, including primary solution lines 112a and 112b, last fill solution line 114, fresh, pre-pump line 116a, fresh pumping segment 118a, fresh, post-pump line 120, inline fluid heating pathway 122, fresh, reusable sub-segment 124f including one-way male luer lock check valve 132, associated "Y" or "T" fittings and pressure pod 130a, is provided within a sealed container 152. The disposable tubing section of disposable set 110b, including patient line 126, drain line 128, used pumping segment 118b, used, disposable sub-segment 124u including female luer lock connector 134, associated "Y" or "T" fitting and pressure pod 130b, is provided within a sealed container 154. Sealed containers 152 and 154 are in one embodiment packaged together in an overpouch 156 and sterilized via steam, gamma radiation or ethylene oxide.

Packaging assembly 150 illustrates a first use assembly in which sealed, sterilized containers 152 and 154 are opened, a cap is removed from female luer lock connector 134 (and possibly from one-way male luer lock check valve 132), after which one-way male luer lock check valve 132 and female luer lock connector 134 are connected to form partially reusable disposable set 110b for use with cycler 20a. In a subsequent treatment, a replacement packaging assembly is opened, wherein the replacement package has only the disposable tubing section of disposable set 110b, including patient line 126, drain line 128, used pumping segment 118b, used, disposable sub-segment 124u including female luer lock connector 134, associated "Y" or "T" fitting and pressure pod 130b provided in sealed container 154. Sealed container 154 may then be provided with a smaller overpouch. For a subsequent treatment, the patient opens the replacement package, removes a cap from new female luer lock connector 134, removes the old female luer lock connector 134 (connected to the heated sealed tubing piece) from the reusable male luer lock check valve 132, and then connects the new female luer lock connector 134 to the reusable male luer lock check valve 132 to form a new disposable set 110b for the next treatment.

Partially reusable disposable set 110b allows the already relatively simple tubing arrangement to be even further optimized to reduce disposable waste and cost. In an embodiment, the reusable tubing section of partially reusable disposable set 110b is used for a set number of treatments after which the reusable tubing section is discarded and a packaging assembly 150 having both sealed, sterilized containers 152 and 154 is opened and used for the next treatment.

Second Cycler Embodiment

Figure 6:
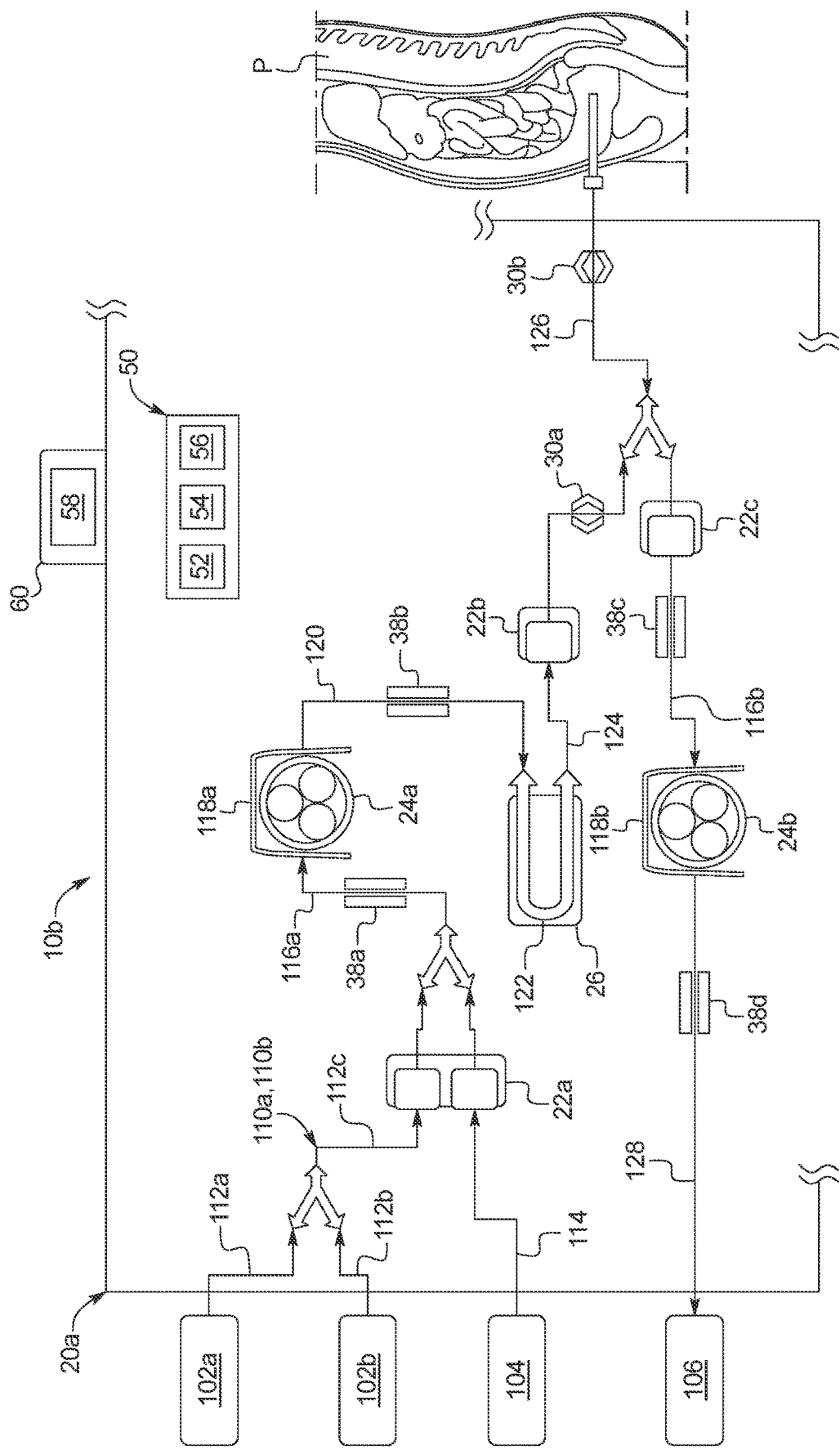
FIG. 6 is a flow schematic view of a second automated peritoneal dialysis ("APD") system of the present disclosure having a dual peristaltic pump arrangement and alternative pressure sensing.
Figure 7:
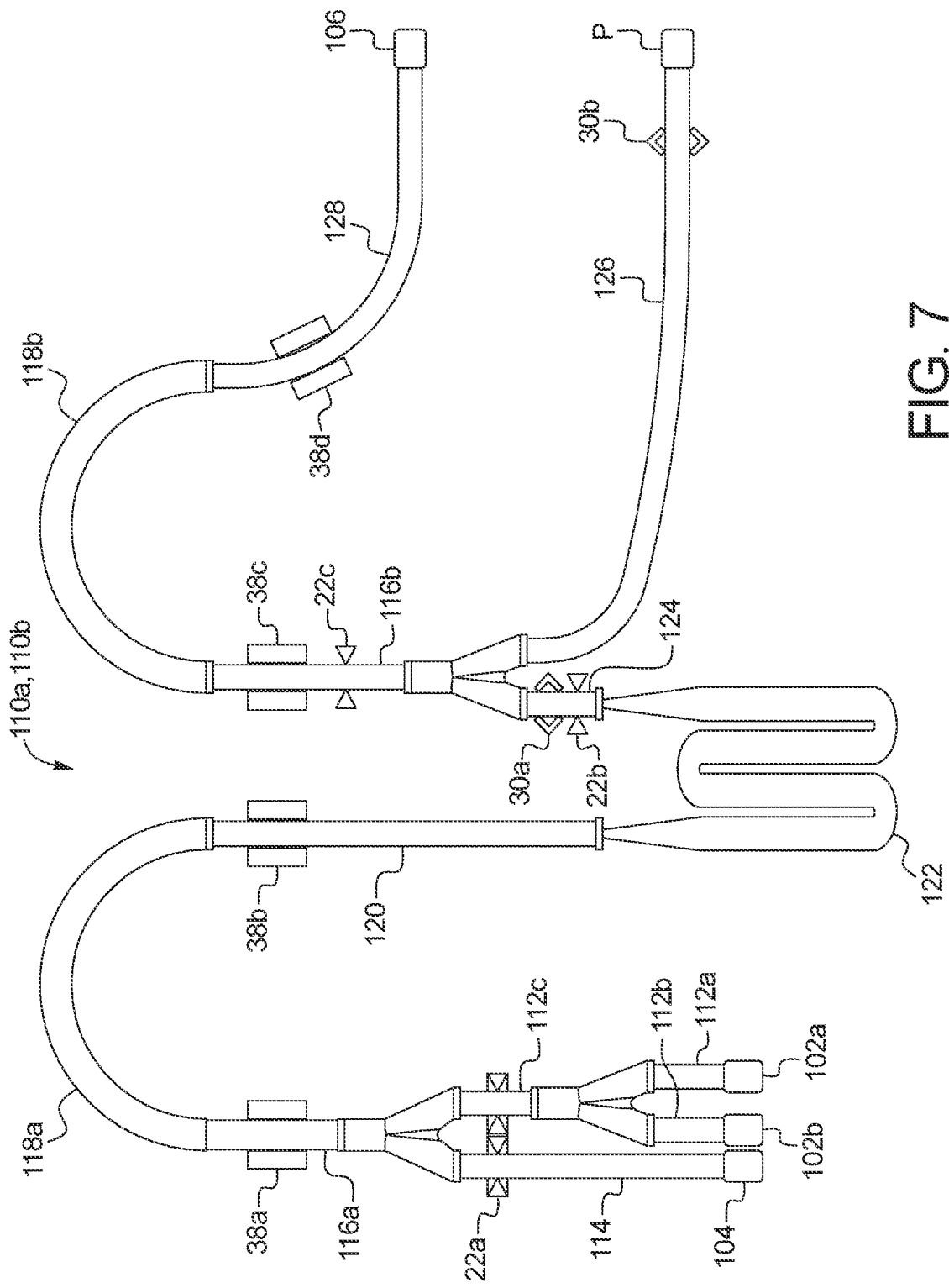
FIG. 7 is an elevation or top plan view of one embodiment of a disposable set useable with the alternative pressure sensing of system of FIG. 6.

Referring now to FIGS. 6 and 7, an alternative APD system 10b having an alternative cycler 20b is illustrated. Cycler 20b of system 10b is configured to operate with either disposable set 110a or 110b described herein. Cycler 20b includes many of the same components as discussed above for cycler 20a. Those components are numbered the same as above for cycler 20b and include all of the structure, functionality and alternatives discussed above for cycler 20a. The primary difference with cycler 20b is that fresh PD fluid pressure transducer 28a and used PD fluid pressure transducer 28b of cycler 20a, which are configured to operate with fresh and used PD fluid pressure pods 130a and 130b, are replaced by non-invasive pressure or force sensors 38a to 38d. Non-invasive pressure or force sensors 38a to 38d are configured to measure the positive or negative forces imparted by the fresh or used PD fluid on the tubes through which the PD fluid flows. Non-invasive pressure or force sensors 38a to 38d have a bracket shape in the illustrated embodiment, which may compress corresponding tubes 116a, 120, 116b and 128 slightly, creating a static force reading against which the measured fluid pressure reading is compared (e.g., additional positive force indicating positive pressure, or additional negative force indicating negative pressure).

Because non-invasive pressure or force sensors 38a to 38d do not require additional disposable components, disposable sets 110a and 110b may be simplified and made more inexpensively by eliminating pressure pods 130a and 130b. Force sensors 38a to 38d may also be provided in greater number, e.g., providing positive and negative pressure data for each pump 24a and 24b (additional pressure sensors 28c and 28d and associated pressure pods 130c and 130d may also be provided for cycler 20a of system 10a if desired). It is also contemplated to provide an additional non-invasive pressure or force sensor (like pressure sensors 38a to 38d) along patient line 126, which measures both positive and negative patient pressures. Such patient line pressure sensor may be provided instead of any one or more of pressure sensors 38a to 38d.

Third Cycler Embodiment

Figure 8:
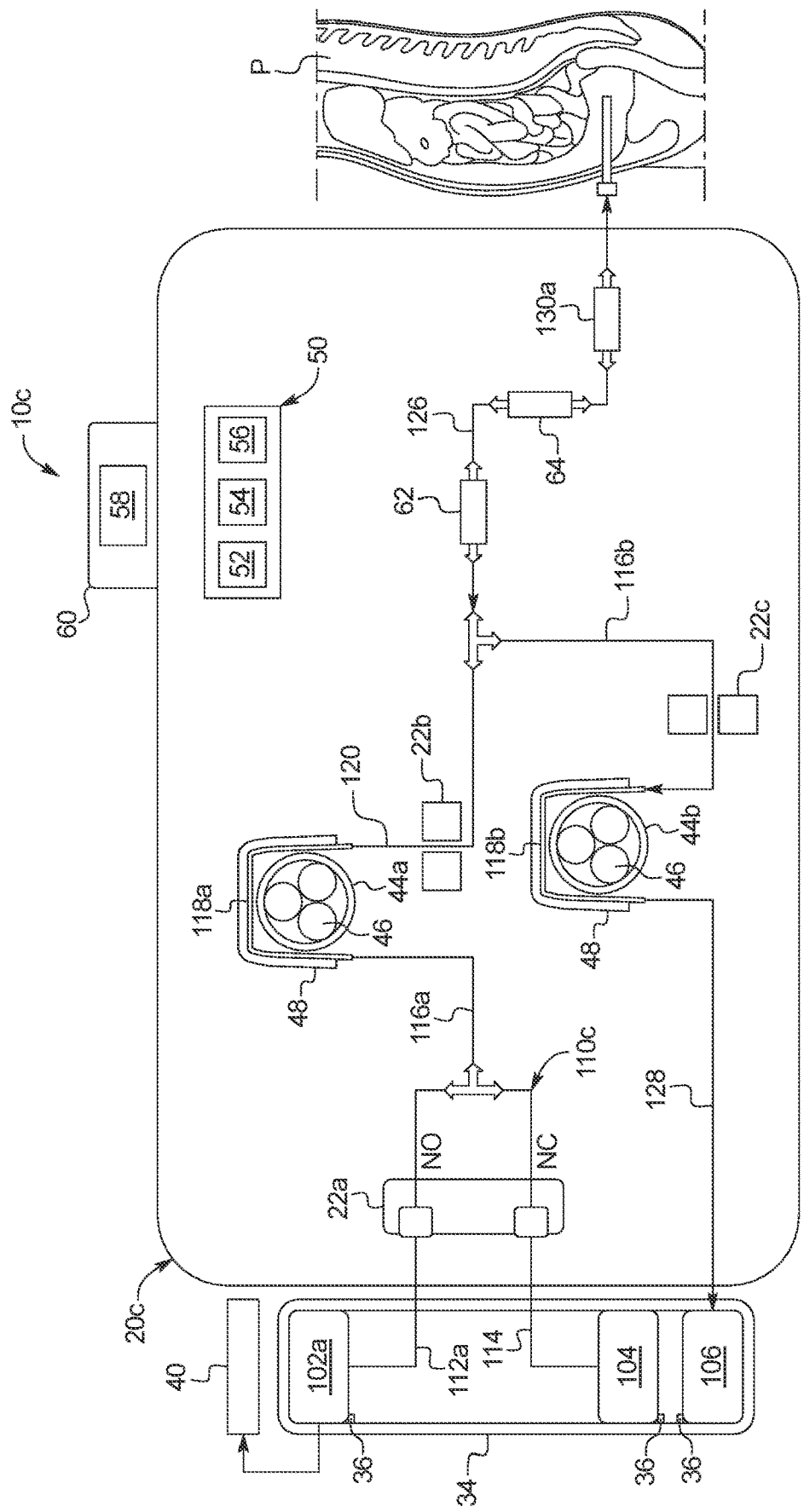
FIG. 8 is a flow schematic view of a third automated peritoneal dialysis ("APD") system of the present disclosure having a batch heater instead of an inline heater and a plurality of disposable flow components.

Referring now to FIG. 8, an alternative system 10c includes alternative cycler 20c under control of control unit 50. Cycler 20c includes many of the same components as discussed above for cycler 20a. Those components are numbered the same as above for cycler 20c and include all of the structure, functionality and alternatives discussed above for cycler 20a. One primary difference with cycler 20c (which may also be used in any of cyclers 20a, 20b and 20d) is that inline heater 26 is replaced with a static heater 34 under control of control unit 50, such as a resistive plate heater. Resistive plate heater 34 may be placed beneath primary fresh PD fluid containers or bags 102a and 102b (only container 102a shown in FIG. 8) and last fill container or bag 104. Resistive plate heater 34 may include an enclosure (not illustrated) in which containers 102a, 102b and 104 are stacked to reduce a footprint of the plate heater. The enclosure may be insulated to efficiently retain heat and help to heat the fluid within each of the containers to body temperature or 37° C. One or more temperature sensor 36 outputting to control unit 50 may be associated with resistive plate heater 34 and/or the enclosure to ensure that the PD fluid (primary or last fill) within each of containers 102a, 102b, 104 is heated to the desired temperature. Control unit 50 in the illustrated embodiment commands a power source 40, which may be located within cycler 20c or within heater 34, to deliver a commanded amount of electrical power to plate heater 34 based on feedback from temperature sensor 36 to achieve the desired PD fluid temperature. Heater 34 may be separate from cycler 20c as illustrated or be provided by cycler 20c, e.g., on the top of the cycler.

Another difference with alternative system 10c and alternative cycler 20c operating with disposable set 110c, which may also be applied to any of systems 10a, 10b and 10d discussed herein, is that one or more components that are normally reusable are made instead to be disposable, or have disposable components, reducing the overall amount of hardware needed in the cycler. In FIG. 8, one such component includes alternative fresh and used PD fluid pumps 44a and 44b under control of control unit 50, which may be peristaltic pumps, wherein pump rollers 46 and raceways 48 are hard plastic, e.g., made of any of the plastics discussed herein, and disposable. Disposable rollers 46 are then coupled to the output shaft of a reusable motor (not illustrated) of cycler 20c for treatment. The disposable peristaltic pumping arrangement thus allows the user to load disposable set 110c for treatment without having to handle peristaltic pump tubing.

Another such component is a primarily disposable flow sensor 62, which as discussed herein may include a disposable rotor, vane or fan blade disposed located along (e.g., spliced into or located within) patient line 126, which spins at a rate dependent on the flowrate of fresh or used PD fluid flowing through patient line 126. The outputs from flow sensor 62 are used by control unit 50 to control the flowrate of fresh and used PD fluid pumped by PD fluid pumps 44a and 44b to desired or specified flowrates (e.g., 50 to 300 milliliters per minute). The outputs from flow sensor 62 are also integrated over time by control unit 50 to yield (i) how much fresh PD fluid is delivered to patient P for each patient fill, (ii) how much used PD fluid is removed from patient P for each patient drain, and (iii) a difference between (ii) versus (i) to know how much ultrafiltration ("UF") or excess water has been removed from the patient.

A further such component may include a primarily disposable conductivity sensor 64 placed along patient line 126, the output of which may be used by control unit 50 to (i) compare against a desired or set conductivity output to ensure that fresh PD fluid is of the prescribed constituency and (ii) measure urea and creatinine levels and potential peritonitis for used PD fluid. Primarily disposable conductivity sensor 64 may include one or more probes, e.g., primarily plastic probes, holding a stainless steel electrode or trace, wherein the probes are built into disposable conductivity sensor 64. The one or more probes may include a separate probe for temperature compensation, wherein the temperature reading may also be used for inline or batch PD fluid temperature control. Primarily disposable conductivity sensor 64 may also present multiple contacts on its outer surface, which are mated with reusable contacts (not illustrated) provided at cycler 20c, thereby further reducing the overall hardware needed at cycler 20c.

A still further primarily disposable component may be a disposable pressure sensor located along patient line 126, which may for example be either of disposable fresh and used PD fluid pressure pods 130a (illustrated) or 130b discussed herein. The output of pressure pod 130a located along patient line 126 is used as feedback to ensure that the positive pressure of fresh PD fluid delivered to patient P from fresh PD fluid pump 44a is within a positive patient pressure limit (e.g., 3.0 psig (0.21 bar) or less). The output of pressure pod 130a in system 10c is also used as feedback to ensure that the negative pressure of used PD fluid removed from patient P via used PD fluid pump 44b is within a negative patient pressure limit (e.g., at or between −1.5 psig (−0.10 bar) and zero psig).

System 10c under control of control unit 50 is illustrated in simplified form in FIG. 8 having a single primary PD fluid container 102a (which may be a large six liter container for example to supply multiple patient fills), wherein that container and last fill container 114 are controlled by three-way valve 22a. Valves 22b and 22c may be two-way valves, wherein valve 22c is closed and valve 22b is opened during patient fills. Valve 22b is closed and valve 22c is opened during patient drains. In any of systems 10a to 10c described herein having two peristaltic pumps, if the peristaltic pumps sufficiently occlude pumping segments 118a and 118b when the pumps are stopped or are not actuated, then valves 22b and 22c may be eliminated, further reducing the amount of cycler hardware. It is also expressly contemplated that disposable or partially disposable PD fluid pumps 44a and 44b, primarily disposable flow sensor 62, and primarily disposable conductivity sensor 64 may be combined and used with the valving, hydraulic layout and inline heating of systems 10a and 10b, the alternative pressure sensing of system 10b, and the single PD fluid pump and alternative valving and hydraulic layout of system 10d.

It is also contemplated to splice fresh, post-pump line 120 in system 10c and place one-way male luer lock check valve 132 in the upstream section of spliced line 120 and to have the downstream section of spliced line 120 terminate with a female luer lock connector 134. In this manner, reusable and disposable tubing sections may be created as discussed above for disposable set 110b. The reusable and disposable tubing sections may be packaged in separate containers as discussed above, wherein replacement package assemblies having only disposable tubing sections are provided for multiple treatments using the reusable tubing section.

Fourth Cycler Embodiment

Figure 9:
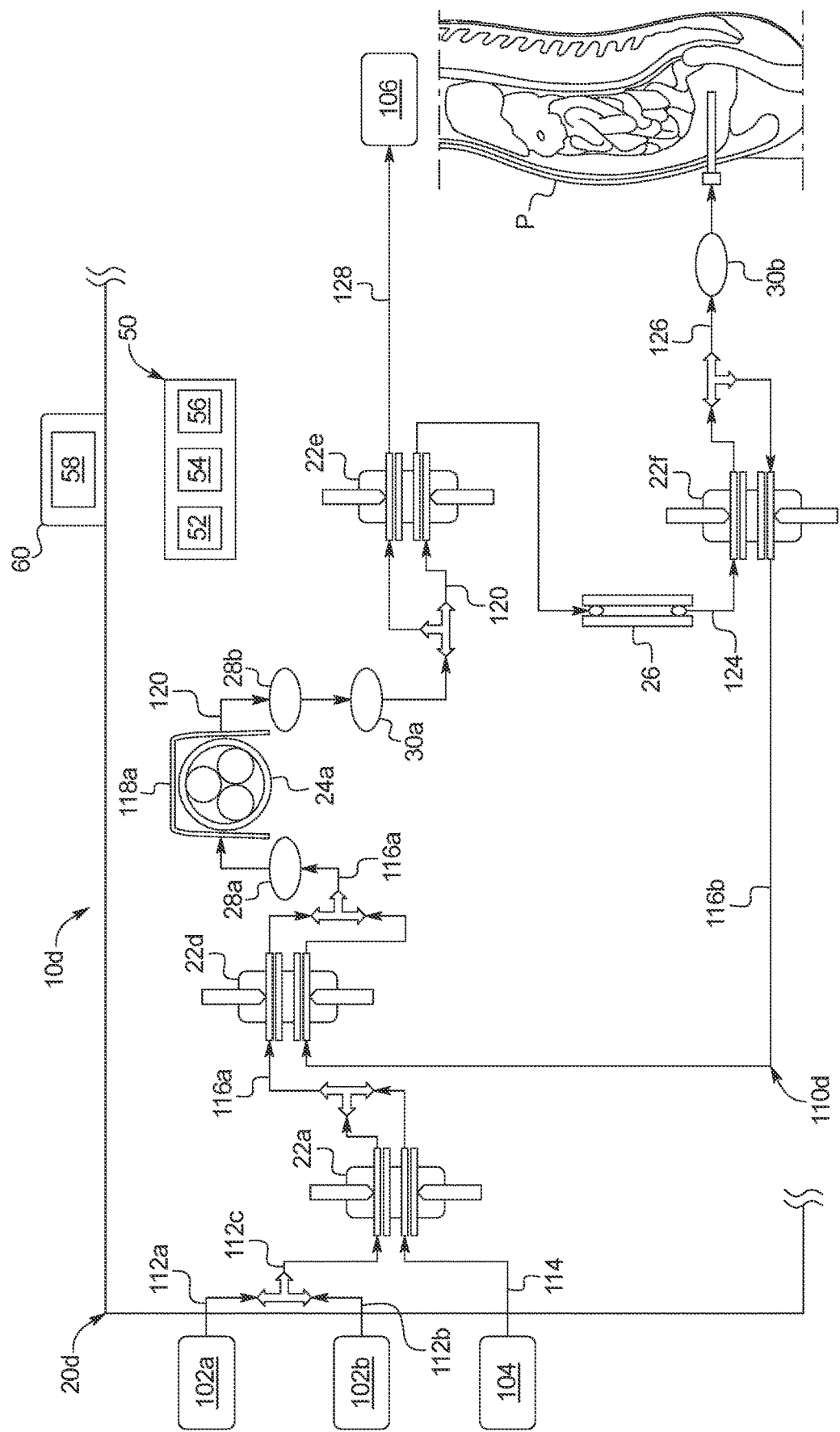
FIG. 9 is a flow schematic view of a fourth automated peritoneal dialysis ("APD") system of the present disclosure having a single peristaltic pump arrangement and alternative pressure sensing.

Referring now to FIG. 9, an alternative system 10*d* includes alternative cycler 20*d* under control of control unit 50. Cycler 20*d* includes many of the same components as discussed above for cycler 20*a*. Those components are numbered the same as above for cycler 20*d* and include all of the structure, functionality and alternatives discussed above for cycler 20*a*. The primary differences with cycler 20*d* are that it includes a single pump 24*a* under control of control unit 50, such as a peristaltic pump. The single pump arrangement necessitates an alternative disposable set 110*d*, which includes a modified flowpath. The modified flowpath is selectively opened and occluded via alternative three-way valves 22*d* to 22*f* under control of control unit, which operate with three-way valve 22*a* described above.

In the illustrated embodiment, three-way valve 22*d* is oriented to allow either the flow of fresh PD fluid through fresh, pre-pump line 116*a* to pumping segment 118*a* or the flow of used PD fluid through used pre-pump line 116*b* to pumping segment 118*a*. Three-way valve 22*e* is oriented to allow either the flow of used PD fluid from pumping segment 118*a*, through drain line 128, to drain container or house drain 106 or the flow of fresh PD fluid from pumping segment 118*a*, through fresh, post-pump line 120, to inline heater 26. Three-way valve 22*f* is oriented to allow either the flow of fresh PD fluid from inline heater 26, through post-heating pathway segment 124, to patient line 126 and patient P or the flow of used PD fluid from patient P and patient line 126, through used pre-pump line 116*b*, back to three-way valve 22*d*.

Cycler 20*d* is shown using pressure sensors 28*a* and 28*b* located upstream and downstream of pumping segment 118*a*, wherein pressure sensor 28*a* measures negative fresh or used inlet pressure (from solution containers or patient P) and positive fresh and used outlet pressure (to patient P or drain). A pressure sensor may alternatively or additionally be located along patient line 126. One or more alternative pressure sensor 38*a* to 38*n* may be used instead, e.g., a single pressure sensor 38*a* located long patient line 126, or multiple pressure sensors 38*a* to 38*n* located at the locations of pressure sensors 28*a* and 28*b* and optionally additionally along patient line 126.

Priming sensor 30*b* is located in the same position as described above for systems 10*a* and 10*b* of FIGS. 1 and 6 and includes all structure and functionality described above. Priming sensor 30*a* is located instead along line 120 for the detection of fresh or used PD fluid downstream from pumping segment 118*a*. System 10*d* may operate alternatively with the batch, resistive plate heating described above, which eliminates inline heater 26. System 10*d* is advantageous because it requires only one pump but can still pump fresh PD fluid to and removed used PD fluid from patient P continuously.

During a patient fill, control unit 50 causes peristaltic pump actuator 24*a* to (i) pull primary fresh PD fluid from one or both of containers 102*a* or 102*b* or last fill fluid from last fill container 104 depending on the orientation of three-way valve 22*a*, and (ii) with three-way valve 22*d* oriented to occlude line 116*b*, three-way valve 22*e* positioned to occlude drain line 128, and three-way valve 22*f* positioned to occlude line 116*b*, pump the fresh PD fluid through lines 116*a*, 120, 124 and patient line 126 to patient P. The patient fill pumping continues for any of systems 10*a* to 10*d* until a prescribed fresh PD fluid or last fill fluid is delivered to the patient. Control unit 50 uses feedback from pressure sensor 28*b* to control peristaltic pump actuator 24*a* such that the positive pumping pressure is below a positive patient pressure limit (e.g., 3.0 psig (0.21 bar) or less).

During a patient drain, control unit 50 causes peristaltic pump actuator 24*a* to (i) pull used PD fluid or effluent from patient P, and (ii) with three-way valve 22*f* oriented to occlude line 124, three-way valve 22*d* oriented to occlude line 116*a*, and three-way valve 22*e* oriented to occlude a downstream portion of line 120, pump the used PD fluid or effluent through patient line 126, line 116*b*, line 116*a*, an upstream portion of line 120 and drain line 128 to drain container or house drain 106. Control unit 50 for any of systems 10*a* to 10*d* may be programmed to end a patient drain when (i) a prescribed amount of used dialysis fluid (e.g., a factor such as 1.3 multiplied by the prescribed fill volume) has been removed from patient P or (ii) a characteristic signal or output from a negative patient pressure sensor (sensor 28*b* for cycler 20*a*, sensor 38*c* for cycler 20*b*, and sensor 28*a* for cycler 20*d*), e.g., a characteristic negative pressure increase, is seen at control unit 50, which indicates that the patient is empty or virtually empty. Control unit 50 uses feedback from pressure sensor 28*a* in system 10*d* to control peristaltic pump actuator 24*a* such that the negative pumping pressure is within a negative patient pressure limit (e.g., at or between −1.5 psig (−0.10 bar) and zero psig). Control unit 50 for any of systems 10*a* to 10*d* determines the amount of ultrafiltration ("UF") removed from patient P one or more times over the course of treatment by subtracting the one or more patient fill volumes from one or more patient drain volumes.

It should be understood that various changes and modifications to the presently preferred embodiments described herein will be apparent to those skilled in the art. For example, any of the three-way valves described herein may be replaced with two, two-way valves. It is therefore intended that any or all of such changes and modifications may be covered by the appended claims.

The invention is claimed as follows:

1. A disposable set for a peritoneal dialysis ("PD") treatment comprising:
 a fresh PD fluid pumping portion;
 a used PD fluid pumping portion;
 a reusable tubing section including the fresh PD fluid pumping portion and a one-way valve, the reusable tubing section terminating at the one-way valve to prevent used PD fluid from entering the reusable tubing section; and
 a disposable tubing section including a "Y" or "T" fitting and the used PD fluid pumping portion, wherein a first end of the "Y" or "T" fitting is configured to fluidly couple to a patient line, a second end of the "Y" or "T" fitting is fluidly coupled to the used PD fluid pumping portion, and a third end of the "Y" or "T" fitting is fluidly coupled to a connector, the connector configured to be connected to the one-way valve to form the disposable set for use in the PD treatment.

2. The disposable set of claim 1, wherein at least one of the fresh PD fluid pumping portion or the used PD fluid pumping portion includes a tubing segment for operation with a peristaltic pump actuator.

3. The disposable set of claim 1, which includes at least one supply line located on an opposing side of the fresh PD fluid pumping portion from the one-way valve.

4. The disposable set of claim 3, which includes a first "Y" or "T" connection between first and second supply lines and a second "Y" or "T" connection between an outlet line of the first "Y" or "T" connection and a third supply line.

5. The disposable set of claim 4, which includes first and second primary fresh PD fluid containers in fluid communication with the first and second supply lines and a last fill fluid container in fluid communication with the third supply line.

6. The disposable set of claim 1, wherein at least one of (i) the reusable tubing section includes a fresh PD fluid pressure sensing area in fluid communication with the fresh PD fluid pumping portion or (ii) the disposable tubing section includes a used PD fluid pressure sensing area in fluid communication with the used PD fluid pumping portion.

7. The disposable set of claim 6, wherein the at least one fresh PD fluid pressure sensing area or the used PD fluid pressure sensing area includes a pressure pod having a diaphragm separating a PD fluid receiving side from an air side of the pod.

8. The disposable set of claim 6, wherein at least one of the fresh PD fluid pressure sensing area is in fluid communication with an outlet of the fresh PD fluid pumping portion, or the used PD fluid pressure sensing area is in fluid communication with an inlet of the used PD fluid pumping portion.

9. The disposable set of claim 1, wherein the reusable tubing section includes an inline fluid heating pathway.

10. The disposable set of claim 9, wherein the inline fluid heating pathway is a serpentine pathway.

11. The disposable set of claim 1, wherein the disposable tubing section includes a drain line in fluid communication with an outlet of the used PD fluid pumping portion.

12. The disposable set of claim 11, which includes a drain container in fluid communication with the drain line.

13. The disposable set of claim 1, wherein the disposable tubing section includes the patient line.

14. The disposable set of claim 1, which includes a packaging assembly including a first sealed container holding the reusable tubing section a second sealed container holding the disposable tubing section.

15. The disposable set of claim 14, which includes a replacement packaging assembly providing the second sealed container but not the first sealed container.

16. A peritoneal dialysis ("PD") system comprising:
a disposable set including
a fresh PD fluid pumping portion,
a used PD fluid pumping portion,
a reusable tubing section including the fresh PD fluid pumping portion and a one-way valve, the reusable tubing section terminating at the one-way valve to prevent used PD fluid from entering the reusable tubing section, and
a disposable tubing section including a "Y" or "T" fitting and the used PD fluid pumping portion, wherein a first end of the "Y" or "T" fitting is configured to fluidly couple to a patient line, a second end of the "Y" or "T" fitting is fluidly coupled to the used PD fluid pumping portion, and a third end of the "Y" or "T" fitting is fluidly coupled to a connector, the connector configured to be connected to the one-way valve to form the disposable set for use in the PD treatment; and
a cycler including
a fresh PD fluid pump operable with the fresh PD fluid pumping portion, and
a used PD fluid pump operable with the used PD fluid pumping portion.

17. The PD system of claim 16, wherein the reusable tubing section includes a fresh PD fluid pressure pod and the disposable tubing section includes a used PD fluid pressure pod, and wherein the cycler includes fresh and used PD fluid pressure transducers operable with the fresh and used PD fluid pressure pods, respectively.

18. The PD system of claim 16, wherein the reusable tubing section includes an inline fluid heating pathway, and the cycler includes an inline heater operable with the inline fluid heating pathway.

19. The PD system of claim 16, wherein the cycler includes at least one priming sensor operable with the disposable tubing section.

20. The PD system of claim 16, wherein the cycler includes at least one first valve operable with the reusable tubing section upstream of the fresh PD fluid pumping portion, the cycler further including at least one second valve operable with the disposable tubing section upstream of the used PD fluid pumping portion.

21. The PD system of claim 16, wherein the cycler includes a flow sensor operable with a patient line portion of the disposable tubing section.

* * * * *